United States Patent [19]
Mukerji et al.

[11] Patent Number: 6,071,718
[45] Date of Patent: Jun. 6, 2000

[54] METHODS OF PRODUCING A RECOMBINANT PROTEIN

[75] Inventors: Pradip Mukerji, Gahanna; Robert George Hards, Delaware; Jennifer Marie Thurmond, Columbus; Amanda Eun-Yeong Leonard, Gahanna, all of Ohio

[73] Assignee: Abbott Laboratories, Abbott Park, Ill.

[21] Appl. No.: 08/757,177

[22] Filed: Nov. 27, 1996

[51] Int. Cl.⁷ .................................................. C12P 21/06
[52] U.S. Cl. .................. 435/69.1; 435/325; 435/252.33; 435/254.11; 435/320.1
[58] Field of Search ................................. 435/69.1, 212, 435/219, 220, 222, 223, 224, 225, 226, 252.3, 252.33, 320.1, 325; 536/23.1, 23.2

[56] References Cited

U.S. PATENT DOCUMENTS

| | | | |
|---|---|---|---|
| 4,543,329 | 9/1985 | Daum et al. | 435/69 |
| 5,013,662 | 5/1991 | Ben-Bassat et al. | 435/212 |
| 5,506,209 | 4/1996 | Mukerji et al. | 514/21 |
| 5,538,952 | 7/1996 | Mukerji et al. | 514/21 |

FOREIGN PATENT DOCUMENTS

| | | |
|---|---|---|
| 32536 | 12/1989 | Australia . |
| 37170 | 4/1990 | Australia . |
| 9627017 | 9/1996 | WIPO . |

OTHER PUBLICATIONS

Mayo et al. "Molecular cloning and sequence analysis of the X–Prolyl dipeptidyl aminopeptidase gene from lactococcus lactice subsp. cermoris" Appl. Environ. Microbiol. 57, 38–44, Jan. 1991.

Ben–Bassat, A. in "Purification and analysis of recombinant proteins", R. Seetharam and S. K. Sharma, Eds., Marcel Dekker, Inc., New York, NY, pp 147–159, 1991.

Greenberg et al., *Journal of Biological Chemistry*, 259:5132–38 (1994).

Hansson et al., *Protein Expression and Purfication*, 4:373–381 (1993).

A. B–Bassat et al., *Journal of Bacteriology*, 169:751–757 (1987).

Lingappa et al., Proceeding of the National Academy of Science USA, 74:2432–2436 (1977).

Hitzeman et al.,*Science*, 219:620–25 (1983).

Klein et al., *Microbiollogy* (1994), 140, 1133–1139.

Leenhouts et al., *Applied and Environmental Microbiology*, 55:2, 394–400, (1989).

Johnson et al., *Bio/Technology*, 12:1357–1360 (1994).

Shen T. –J. et al., Proceedings of the National Academy of Sciences of USA, vol. 90, Sep. 1993, pp. 8108–8112—XP002058672.

Sabin E. A. et al., "High–Level Expression and In Vivo Processing of Chimeric Ubiquitin Fusion Proteins In Saccharomyces Cerevisiae", vol. 7, No. 7, Jul. 1989, pp. 705–709, XP000034178.

*Primary Examiner*—Robert A. Wax
*Assistant Examiner*—Nashaat T. Nashed
*Attorney, Agent, or Firm*—Cheryl L. Becker

[57] ABSTRACT

The subject invention relates to methods of processing and producing recombinant proteins in vivo, for example, recombinant phosphorylated beta-casein. The subject invention also relates to the proteins produced by these methods as well as to uses of these proteins.

18 Claims, 16 Drawing Sheets

HUMAN MILK BETA-CASEIN
Arg-Glu-Thr-Ile-Glu-Ser-Leu-Ser-Ser-Ser...

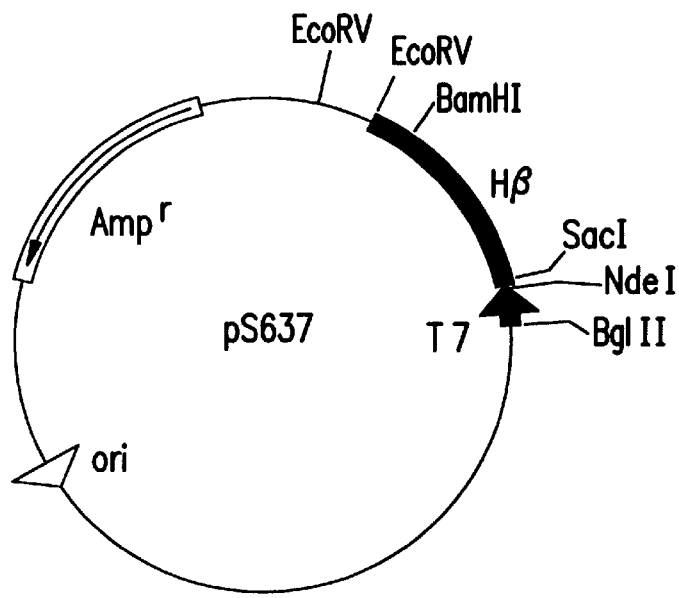
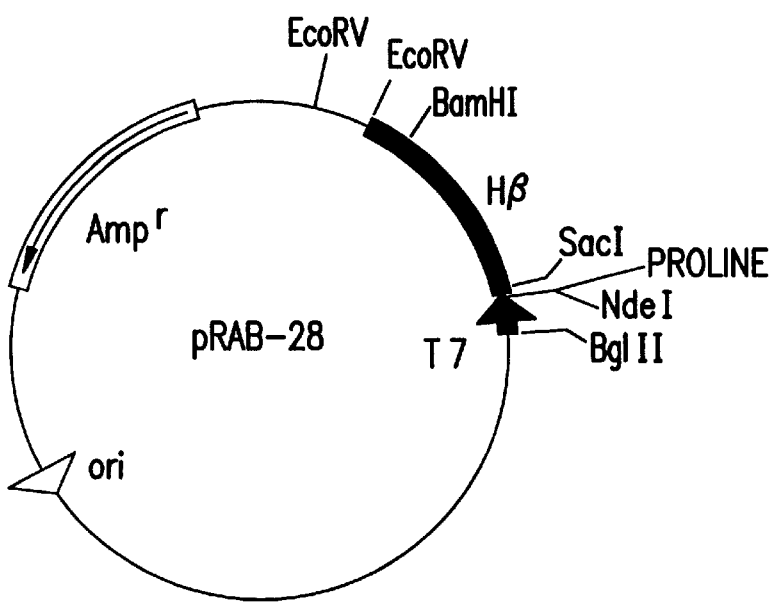
FIG.3

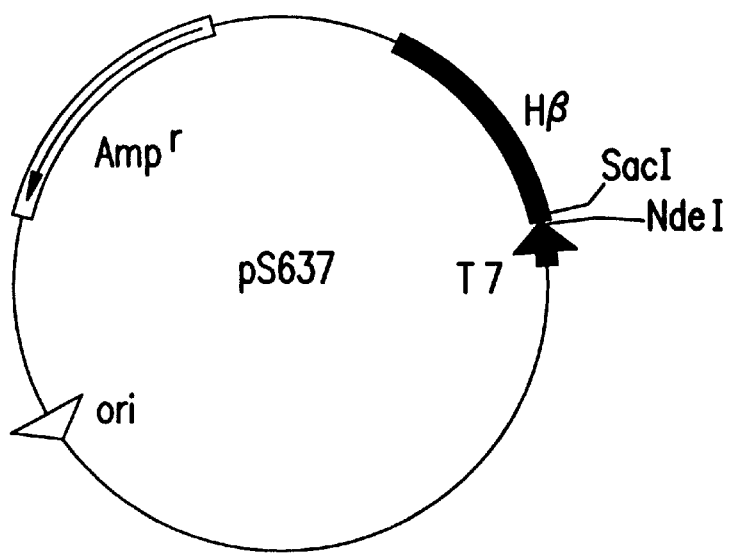
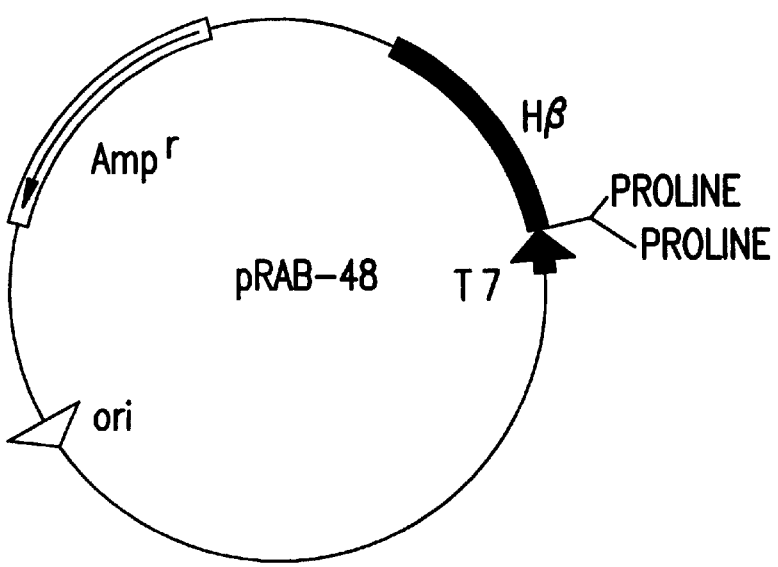
FIG.5

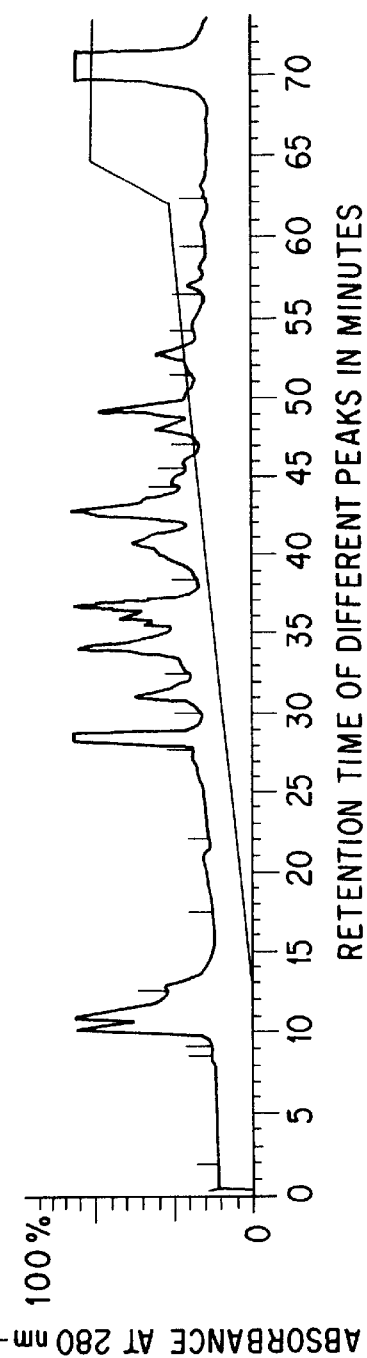
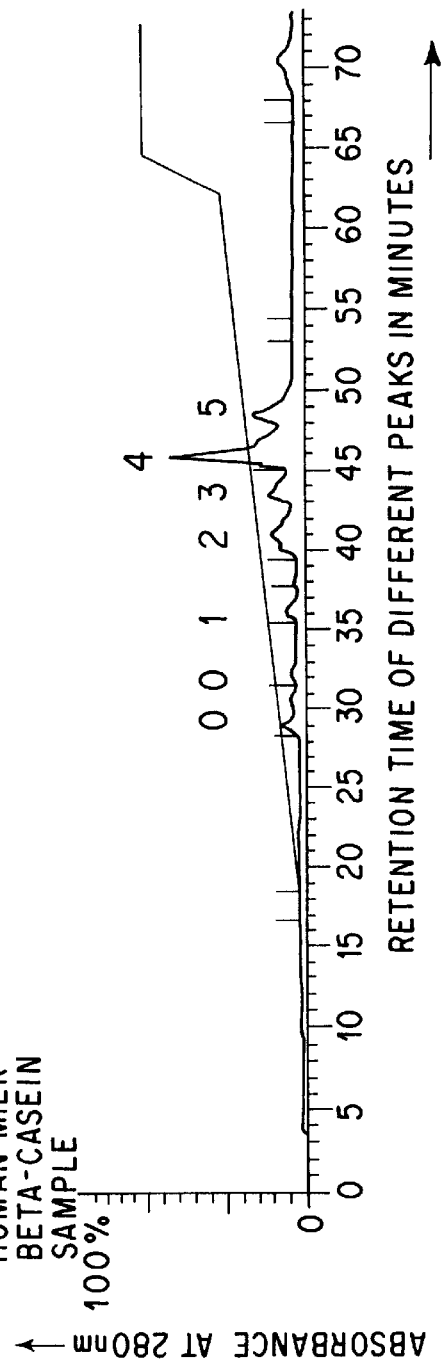

```
                          SEQUENCE LISTING (1) GENERAL INFORMATION:

(iii) NUMBER OF SEQUENCES:    16

(2) INFORMATION FOR SEQ ID NO:1:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:1:

Met Pro Arg Gln
1

(2) INFORMATION FOR SEQ ID NO:2:

(i) SEQUENCE CHARACTERISTICS:
         (A) LENGTH: 32 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:2:

TATGCCGCGT GAAACCATCG AATCCCTGAG CT                                   32

(2) INFORMATION FOR SEQ ID NO:3:

(i) SEQUENCE CHARACTERISTICS:
         (A) LENGTH: 26 nucleic acids
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:3:

CAGGGATTCG ATGGTTTCAC GCGGCA                                          26
```

(2) INFORMATION FOR SEQ ID NO:4:

(i) SEQUENCE CHARACTERISTICS:
        (A) LENGTH: 5
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Pro Pro Arg Gln
1               5
```

(2) INFORMATION FOR SEQ ID NO:5:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:5:

```
Pro Pro Arg Glu
1
```

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

TATGCCGCCG CGTGAAACCA TCGAATCCCT GAGCT                    35

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

CAGGGATTCG ATGGTTTCAC GCGGCGGCA                        29

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

TCAGAGGAAT TCAAGATGCA AATCACAGAA AAATA                    35

(2) INFORMATION FOR SEQ ID NO:9:

(i) SEQUENCE CHARACTERISTICS:

```
            (A) LENGTH: 35 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:9:

GTGTCCGTCG ACCTAGTCCT GGCTGATTAA CCAGT                                    35

(2) INFORMATION FOR SEQ ID NO:10:

(i) SEQUENCE CHARACTERISTICS:
            (A) LENGTH: 39 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:10:

AAAGTAGGAT CCTGTTTATT ACGGAGGATT TAAAATGCG                                39

(2) INFORMATION FOR SEQ ID NO:11:

(i) SEQUENCE CHARACTERISTICS:
            (A) LENGTH: 39 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:11:

GTCGCGGTCG ACTTAATTTT TCACACTTTC AATAGGAAT                                39

(2) INFORMATION FOR SEQ ID NO:12:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:12:

Arg Gln Thr Ile Gln
1               5

(2) INFORMATION FOR SEQ ID NO:13:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:13:

Arg Gln Thr Ile Gln Ser
1               5

(2) INFORMATION FOR SEQ ID NO:14:

(i) SEQUENCE CHARACTERISTICS:
            (A) LENGTH: 5 amino acids
            (B) TYPE: amino acid
```

-continued

```
        (C) STRANDEDNESS: single
        (D) TOPOLOGY: linear (ii) MOLECULE TYPE: protein (xi) SEQUENCE DESCRIPTION: SEQ ID NO:14:

Pro Arg Gln Thr Ile
1               5

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Arg Glu Thr Ile
1

(2) INFORMATION FOR SEQ ID NO:16:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Glu Thr Ile Ser Ser
1               5
```

METHODS OF PRODUCING A RECOMBINANT PROTEIN

BACKGROUND OF THE INVENTION

1. Technical Field

The subject invention relates to methods of processing and producing recombinant proteins in vivo, for example, recombinant phosphorylated human beta-casein. The subject invention also relates to the proteins produced by these methods as well as to uses of these proteins.

2. Background Information

It is generally recognized that human milk is the best nutritional source for human infants. Human milk is not only an ideal source of nutrients for the developing infant, but it also contains immunoglobulins as well as non-immunological factors that protect the infant from infection by various microorganisms. Human milk is also easily digestable and is less likely to cause allergic reactions than infant formulae based on bovine milk.

Human milk differs from bovine milk, as well as the milk of other mammalian species, in various ways. In particular, overall protein content differs between human milk and bovine milk. Furthermore, bovine milk contains five caseins (i.e., 2 alpha-caseins, 1 beta-casein, 1 kappa-casein and 1 gamma-casein). In contrast, human milk contains only beta- and kappa-casein. Additionally, the amino acid sequences of human milk proteins differ from that of other mammalian milk proteins.

Efforts have been made to develop infant milk formulae that have some of the advantageous properties of human milk, yet which avoid the disadvantages associated with bovine milk based infant formulae such as, for example, allergic reactions and incomplete digestion by the infant. A desirable method to achieve this goal is to add some of the known constituents of human milk, including human milk proteins in their native form, to infant formulae. The human caseins represent important substances, which if added in their native form to infant formulae, would serve to enhance the nutritional value of the formulae and reduce the inherent disadvantages of non-human milk proteins. Human milk casein has also been credited with enhancing calcium absorption, inhibiting angiotensin I-converting enzyme, being an opioid agonist, and exhibiting immunostimulating and immunomodulating effects.

Furthermore, in addition to being a source of amino acids necessary for the synthesis of proteins required for the growth and development of infants, human milk is recognized as containing proteins, including casein, that have other important biological functions. Beta-casein, mentioned above, for example, is one of the most abundant milk proteins synthesized in the mammary gland. After post-translational modification in the Golgi apparatus, the protein is secreted as large calcium-dependent aggregates called micelles. Beta-casein is not a single entity. Rather, it is a heterogeneous group of phosphoproteins secreted during lactation in response to lactogenic hormones.

The primary structure of human beta-casein was determined by Greenberg et al. (*Journal of Biological Chemistry* 259:5132–38 (1984)). Human casein consists largely (>80%) of the beta-form with a smaller amount in the kappa-form. Native beta-casein is a 25 kDa protein. In human milk, beta-casein molecules show variable degrees of post-translational phosphorylation ranging from zero to five phosphate groups per polypeptide chain (FIG. 1; Greenberg et al., supra (1984); Hansson et al., *Protein Expression and Purification* 4:373–81 (1993)). Phosphate groups in the native protein are attached to serine and threonine residues located near the amino terminus (Greenberg et al., supra (1984)). Human and bovine beta-casein exhibit 47% identity in their amino acid sequences.

In view of the benefits of beta-casein, it would be quite beneficial, as noted above, to add this protein to infant formulae or other nutritional formulae. Thus, methods must be devised to create and express this protein and, in particular, beta-casein, recombinantly. Yet, in the expression of proteins in bacterial systems, proteins are obtained which may be lengthened at the N-terminus by a methionine residue.

In a significant fraction of mature cytosolic proteins in bacteria, the N-terminal methionine is cleaved off by a methionine aminopeptidase whose specificity is dependent on the identity of the adjacent amino acid residue (Ben-Bassat et al., *Journal of Bacteriology* 169:751–57 (1987)). In the case of recombinant human beta-casein production in *E. coli*, the extra N-terminal methionine is not cleaved from the adjacent arginine residue by this peptidase (Hansson et al., supra (1993)). Since the methionine can be oxidized to sulfonyl methionine during purification, and this event can increase the immunogenicity/allergenicity of the protein, removal of this terminal methionine is desirable.

One method of generating recombinant protein with a desired N-terminal residue is to express the protein fused to a signal peptide at the N-terminus. This method leads to export, cleavage of the signal peptide, and accumulation of the processed, native protein in the periplasmic space of gram-negative bacteria or in the cytosol of gram-positive bacteria. The protein may be secreted and/or accumulated in the cytosol in yeast, fungi or mammalian cells. However, specificity of the peptidase cleaving the signal peptide may result in heterogeneity at the N-terminus (Lingappa et al., *Proceeding of the National Academy of Science USA*, 74:2432–36 (1977); Hirtzman et al., *Science* 219:620–25 (1983)). Also, there can be a significant quantity of residual cytosolic protein in which the signal peptide is not cleaved.

Another method of removing N-terminal methionine from a recombinant protein is to use purified aminopeptidases (e.g., methionine aminopeptidase, aminopeptidase M, dipeptidyl aminopeptidase) for in vitro processing of the purified recombinant protein (reviewed by Ben-Bassat in *Purification and Analysis of Recombinant Proteins*. eds. R. Seetharam and S. K. Sharma, pp.148–59, Marcel Dekker Inc., N.Y. (1991)). However, this method requires multiple purification steps and may not be economical for large-scale production.

Also, a process to produce proteins which begin at the N-terminus with proline has been described in German Patent Application P 38 11 921.8. This process involves enzymatic cleavage with aminopeptidase-P. Additionally, proline iminopeptidase has also been used in order to liberate a desired protein as described in Australian Patent Application AU-A-37170/89. Both of these processes are quite distinct from that described in the present invention. In fact, the present invention overcomes many disadvantages of these two methods, the methods described above, as well as all such methods utilized in the past.

SUMMARY OF THE INVENTION

The present invention includes a method of producing a recombinant protein in vivo. This method comprises the steps of: a) creating a vector comprising: i) a nucleic acid sequence encoding a protein and ii) a nucleic acid sequence encoding a peptidase, wherein the protein comprises at least one N-terminal amino acid not present in said protein's native form and wherein said nucleic acid sequence encoding the protein is operably linked to a promoter; b) introducing the vector into a host cell under time and conditions sufficient to allow for expression of the recombinant protein, wherein the host cell encodes an endogenous peptidase which cleaves one or more of the N-terminal amino acids of the protein.

In the above described method, the peptidase encoded by the nucleic acid sequence in step (a) may be, for example, iminopeptidase or aminopeptidase. The iminopeptidase may be encoded by a gene referred to as pepI, and the aminopeptidase may be encoded by a gene referred to as pepXP. The endogenous peptidase may be, for example, methionine aminopeptidase. The recombinant protein produced may be, for example, a milk protein, insulin or a growth stimulating factor. An example of such a milk protein that may be produced using the methods of the present invention is recombinant phosphorylated human beta-casein. The host cell used in the methods of the present invention may be, for example, a eucaryotic cell or a procaryotic cell. An example of a procaryotic cell which may be utilized in the methods of the present invention is *Escherichia coli*. The N-terminal amino acid may be, for example, methionine or proline.

The present invention also encompasses recombinant proteins produced according to the methods of the present invention such as, for example, recombinant phosphorylated human beta-casein.

Further, the present invention includes a vector comprising a) a nucleic acid sequence encoding a protein and b) a nucleic acid sequence encoding a peptidase, wherein the protein comprises at least one N-terminal amino acid not present in the protein's native form and wherein the nucleic acid sequence encoding the protein is operably linked to a promoter. The "at least one N-terminal amino acid" may be, for example, methionine or proline. The vector may be, for example, a plasmid, a bacteriophage or a cosmid.

Additionally, the present invention also encompasses a host cell transformed with a vector comprising a) a nucleic acid sequence encoding a protein and b) a nucleic acid sequence encoding a peptidase, wherein the protein comprises at least one N-terminal amino acid not present in said protein's native form and wherein the nucleic acid sequence encoding the protein is operably linked to a promoter, and wherein the host cell encodes an endogenous peptidase. The peptidase encoded by the nucleic acid sequence may be, for example, iminopeptidase or aminopeptidase. The iminopeptidase may be encoded by gene pepI,, and the aminopeptidase may be encoded by gene pepXP. The endogenous peptidase may be, for example, methionine aminopeptidase. The host cell may be, for example, a eucaryotic cell or a procaryotic cell. As noted above, *Escherichia coli* is an example of a procaryotic cell which may be utilized in the present invention. The at least one N-terminal amino acid may be, for example, methionine or proline.

Furthermore, the present invention also includes an infant formula or medical nutritional comprising a recombinant protein produced using the methods of the present invention.

All U.S. patents and publications referred to herein are hereby incorporated in their entirety by reference.

BRIEF DESCRIPTION OF THE DRAWINGS

FIG. 3 is an illustration of the vector pRAB-28 showing the addition of the codon for proline in the gene encoding for recombinant human beta-casein.

FIG. 5 is an illustration of the vector pRAB-48 showing the addition of two codons for proline as the second and third amino acids after methionine in the gene encoding for recombinant human beta-casein.

FIG. 13 illustrates the various phosphoforms of recombinant human beta casein produced from co-expression of constructs pRJB-26/pRAB-51. There are peaks obtained from recombinant beta-casein preparation which have the same retention time as the six different phosphoforms of beta-casein found in milk.

DETAILED DESCRIPTION OF THE INVENTION

Figures 1, 2:
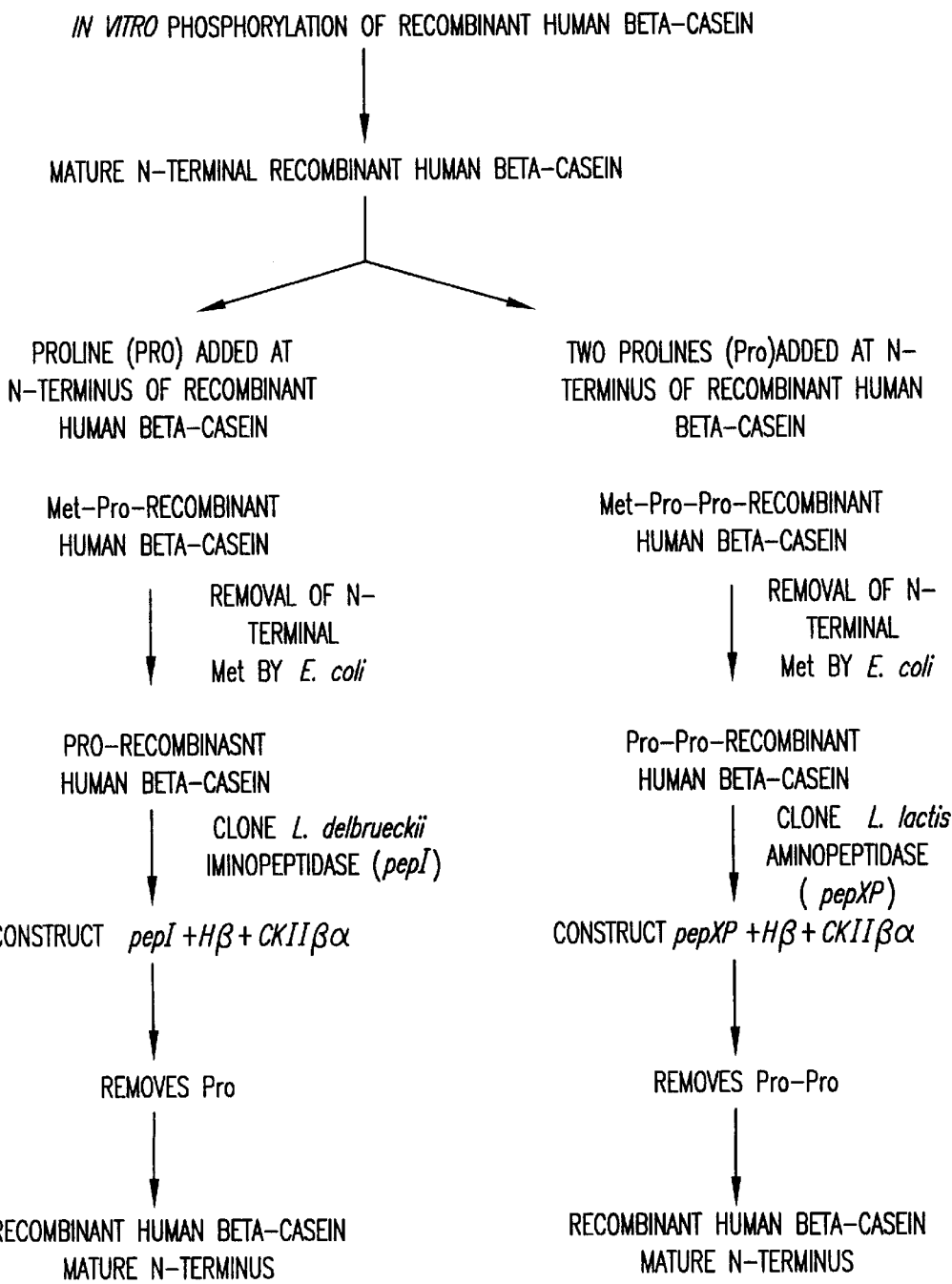
FIG. 1 illustrates the first ten amino acids of beta-casein as it is found in human milk with the phosphorylated residues shown in boldface.
FIG. 2 illustrates the methods or processes of the present invention. Human beta casein is designated HB, and human casein kinase II is denoted as CKIIβα

As stated above, the subject invention relates to methods of producing recombinant proteins in a host cell as well as to the resulting proteins and to uses of these proteins. More specifically, the present invention encompasses methods for producing recombinant human proteins, such as human beta-casein, in procaryotic cells wherein the resultant proteins have amino acid sequences which are identical to those found in the native proteins.

In particular, the subject invention relates to the processing and production of proteins, for example, recombinant phosphorylated human beta-casein protein, in vivo. This is achieved by creating a vector which comprises a nucleic acid sequence encoding the protein of interest as well as a nucleic acid sequence encoding, for example, a heterologous enzyme, for example, a peptidase. The protein includes at least one N-terminal amino acid not present in the protein's native form. Additionally, at least one promoter is utilized to regulate both sequences. The vector is then introduced into a host cell. The cleavage activity of an enzyme encoded by the host cell, for example, methionine aminopeptidase (MAP), is used to process the N-terminal sequence of the protein in addition to the peptidase present in the vector. The beta-casein protein produced by the present methods is identical to that found in human breast milk and can be added, for example, to infant formulae.

The properties of the elements used in the methods of the invention are described, in general, directly below and will be described in more detail subsequently in the application:

Proteins:

A gene sequence encoding a particular protein is engineered such that three or more nucleotides are added to the nucleic acid sequence encoding the protein. These three or more nucleotides encode one or more specific amino acids. Subsequent to translation, the heterologous protein has an altered N-terminus which contains one or more added amino acids. These amino acids correspond to the cleavage site(s) of one or more peptidases encoded by the host cell.

Vectors (Constructs):

The vector used to transform the host cell comprises a gene sequence encoding the heterologous protein as well as a gene sequence encoding a heterologous peptidase. The heterologous peptidase cleaves one or more amino acids of the translated protein subsequent to cleavage by the peptidase of the host cell Host Cells:

The host cell, in which expression of the protein occurs and into which the vector is inserted, possesses endogenous enzymatic activity such that the translated protein is enzymatically modified within the host cell itself. The host cell may be procaryotic or eucaryotic in nature.

The Methods:

As noted, the components described above are used in methods of the present invention, methods comprising the following basic steps: 1) a nucleotide sequence encoding a protein containing additional amino acids at its N-terminus as well as a nucleotide sequence encoding a peptidase are inserted into a construct or vector; 2) the construct or vector is inserted into a host cell possessing endogeneous peptidase activity; 3) during growth and subsequent induction of protein expression, the heterologous protein having the altered N-terminus is produced; 4) the host endogenous peptidase cleaves, for example, the first amino acid at the N-terminus of the heterologous protein creating the amino acid recognition site for the heterologous peptidase; and 5) the second or next amino acid in the N-terminus is then cleaved by the heterologous peptidase, thereby yielding a recombinant human protein with an amino acid sequence that is identical to the native human protein.

The methods of the present invention, as well as the individual steps comprising these methods, are described in detail below:

Creation of Construct (Vector) Containing the Nucleotide Sequence Encoding the Protein First, the nucleotide sequence encoding the protein of interest is identified and isolated. Suitable proteins include any protein having, for example, the following properties: 1) the protein is of procaryotic or eucaryotic origin; 2) the N-terminal amino acid is not methionine; 3) the native protein is synthesized with a peptide sequence at the N-terminus that is subsequently removed by endogenous proteases in the cytoplasm; and 4) the native protein is a secretory protein synthesized with a signal peptide sequence which is removed by cellular proteases prior to secretion.

Nucleotides (i.e., three or more) are then added to the nucleotide sequence encoding the protein by standard genetic engineering techniques (Sambrook et al., *Molecular Cloning: A Laboratory Manual,* 2nd edition. Cold Spring Harbor Press. New York, 1989). These nucleotides encode one or more amino acids (at the amino- or N-terminus of the protein) which may be cleaved by the activity of the heterologous enzyme, the nucleotide sequence of which is placed in a construct (e.g., a plasmid, a bacteriophage, or a cosmid) along with the nucleotide sequence of the modified protein. One of these amino acids may also be cleaved by the endogenous enzyme encoded by the host cell.

The nucleotides and thus ultimate amino acids which are added to the genetic sequence encoding the protein include, for example, one or more of the following: methionine, proline, alanine, and glycine. Preferably, methionine and/or proline are the added amino acids for purposes of the present invention.

The selection of which amino acids to add to the N-terminus of the desired protein depends upon the cleavage characteristics of the enzyme encoded by the sequence inserted into the construct as well as the cleavage characteristics of the endogenous enzyme possessed by the host cell. One must consider, for example, the cleavage specificity of the endogenous enzyme (e.g., methionine aminopeptidase (MAP)), the availability of a protease specific for cleavage of, for example, the second amino acid, and the feasibility of cloning the protease gene. For example, as will be illustrated below, one may use the amino acid sequence Met-X-Pro with the gene pepXP, provided MAP cleaves Met from Met-X.

Once the nucleotide sequence encoding the modified protein is inserted into the construct and is operably linked to a promoter, the nucleotide sequence encoding a particular heterologous enzyme is then inserted into the construct. Suitable heterologous enzymes include, for example, peptidases, and preferably, iminopeptidases and aminopeptidases. More preferably, iminopeptidase from *L. delbrueckii* or aminopeptidase from *L. lactis* is utilized. The gene encoding the former is referred to as pepI, and the gene encoding the latter is referred to as pepXP for purposes herein. Use of iminopeptidases is restricted to proteins which have the N-terminal sequence: $NH_2$-Met-Pro . . . , whereas aminopeptidases may be used for proteins having the N-terminal sequence $NH_2$-Met-X-Pro. Other aminopeptidases may be used with Met-X proteins. Of course, other enzymes functioning in the same manner as the iminopeptidases and aminopeptidases (i.e., possessing the same cleavage specificities) may also be used for purposes of the present invention.

Suitable promoters include at least one promoter which has the ability to regulate the gene encoding the modified protein of interest and the gene encoding the heterologous enzyme of interest. Such promoters may be readily determined by those of ordinary skill in the art. Examples of promoters which may be utilized in the present invention include but are not limited to λP$_L$, Ptac, T7, SP6 and T3. Preferably, T7 and/or Ptac may be utilized.

Furthermore, one or more constructs may be added to the host cell in order to produce the recombinant protein of interest. Preferably, only one construct is utilized. When two constructs are used, two antibiotics, for example, are necessary to maintain the constructs in the host cell, thereby increasing costs with respect to large scale fermentation. This concept will be discussed in more detail below.

Additionally, it is important to note that virtually any recombinant protein may be made using the methods of the present invention. Recombinant human beta-casein has been discussed above. However, other recombinant proteins which may be produced using the methods of the present invention include, for example, insulin, growth factors, and human milk proteins.

Host Cells:

Once the construct has been created, it is then introduced into a suitable host cell by techniques known in the art (see e.g., Sambrook et al., supra (1989)). Suitable host cells preferably provide high efficiency removal of, for example, methionine from the protein and also contain a selectable marker such as, for example, kanamycin or tryptophan. Examples of host cells which may be utilized in the methods of the present invention include procaryotic cells such as, for example, Escherichia sp., Lactobacillus sp., and Bacillus sp., eucaryotic cells such as, for example, Saccharomyces sp., Hansenula sp., and mammalian cells. A type of mammalian cell which may be utilized, for example, is Chinese Hamster Ovary (CHO) cells. Preferably, *Escherichia coli* cells are used.

As noted above, the host cell must encode a peptidase which has the capability to cleave one or more of the added amino acids of the modified protein, such that the ultimate protein of interest is obtained. When using *E. coli*, all cells should have methionine aminopeptidase (MAP) activity. Other procaryotic and eucaryotic cells have been reported to be MAP+; however, any cell lysate may be tested for MAP activity by one of ordinary skill in the art by use of a synthetic substrate (Ben-Bassat et al., supra (1987)). Furthermore, other host cells encoding one or more endogenous peptidases specific for cleavage with respect to a particular amino acid sequence may also be utilized.

Once the host cell expresses the desired protein, for example, recombinant beta-casein, the protein may be purified and added to products of interest. For example, as noted above, recombinant beta-casein, produced by the methods of the present invention, may be added to infant formulae or to medical nutritional products. Since the recombinantly produced protein has an amino acid sequence identical to that found in the native protein, the incidence of allergic reactions should decrease as compared to the incidence of allergic reactions from formulae or products which are based upon the proteins found in bovine milk. Thus, for example, women who choose not to breast feed their newborns will still be able to provide their infants with the benefits of breast milk without increasing the risk of allergic responses by giving their infant a formula containing one or more recombinant proteins produced by the methods of the present invention (see U.S. Pat. Nos.5,506,209 and 5,538, 952).

There are many other benefits to the methods of the present invention as well. For example, the method may be used to change the DNA coding sequence for any recombinant protein such that codons are incorporated for additional amino acid(s) at the N-terminus thereby allowing the "new" or modified protein to be cleaved by the peptidase incorporated in the same construct. Thus, a protein having the desired N-terminus may be produced in one step with a single fermentation.

The present methods also permit large scale, commercial production of the recombinant protein of interest, having the desired N-terminus. Such large scale production often has the benefits of reducing costs and maximizing efficiency.

Furthermore, as noted above, only a single fermentation is required; thus, no modifications, such as in vitro enzymatic treatment through a post-fermentation step, are required to produce the desired protein.

Additionally, since only one construct or vector is used, only one gene encoding one antibiotic is necessary in order to maintain the vector in the host during fermentation. Thus, the use of only one antibiotic decreases the cost of large scale fermentation significantly. This provides an improvement over the previous methods of using two plasmids. More specifically, to maintain two plasmids in a host such as, for example, *E. coli*, selective pressure, such as antibiotic resistance, must be used. Two antibiotics are therefore needed in a fermentation causing an increase in cost, as compared to the methods of the present invention.

The present invention may be further illustrated by the use of the following nonlimiting examples:

EXAMPLE I

N-Terminus Engineering of Heterologous Protein in *E. coli*

The recombinant human beta-casein from the construct pRJB-9 contains an additional methionine at the N-terminus of the gene compared to the human milk beta-casein which contains the N-terminus of arginine. In order to make the recombinant protein identical to that found in mother's milk, the methionine had to be processed. If the amino acid proline is added to the protein after methionine (i.e., between methionine and arginine), the *E. coli* methionine aminopeptidase will cleave methionine from proline. The iminopeptidase derived from the pepI of *L. delbrueckii* will cleave after the N-terminal proline (FIG. 2). Thus, intermediate construct, pRAB-28 (FIG. 3), was created by using a synthetic linker RO77/78

5'--TATGCCGCGTGAAACCATCGAATCCCTGAGCT--3' (see SEQ ID NO:2)

3'--ACGGCGCACTTTGGTAGCTTAGGGAC--5' (see SEQ ID NO:3)

to add an additional codon for proline as the second amino acid in the encoded protein (note: sequence for proline is underlined). The linker was treated with kinase, then cloned into pS637 at the NdeI/SacI sites. The new clone was sequenced using the ABI 373A Automated DNA Sequencer (Applied Biosystems Inc., Foster City, Calif.) to verify the presence of the codon for proline.

Figure 4:
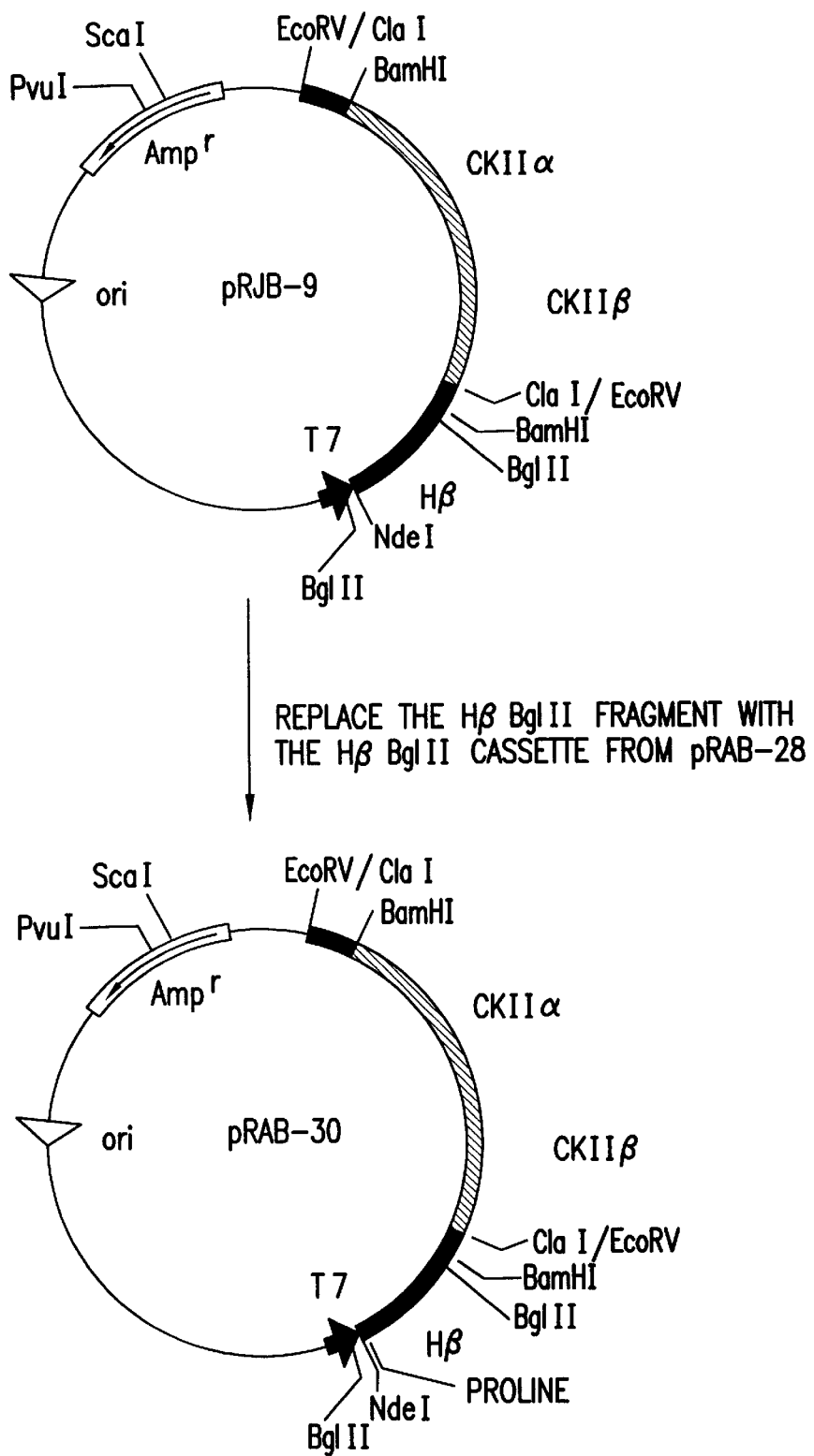
FIG. 4 is an illustration of the vector pRAB-30 where the coding sequence for Met-Pro-Arg-Glu . . . (see SEQ ID NO:1) in recombinant human beta-casein was linked to the human casein kinase II (CKIIβα) gene.

The BglII fragment of the construct pRJB-9 was replaced with the BglII fragment containing the extra codon for proline from pRAB-28. The new construct containing the ampicillin resistance gene, CKIIβα gene and the human beta-casein gene with the coding sequence of Met-Pro-Arg-Glu . . . (see SEQ ID NO:4) was designated as pRAB-30 (FIG. 4).

In addition to the above strategy, a second strategy for producing the properly processed beta-casein was to synthesize a modified human beta-casein gene sequence which would encode a protein with the N-terminal sequence of 5' Met-Pro-Pro-Arg-Glu . . . (see SEQ ID NO:4). When the *E. coli* endogenous methionine aminopeptidase cleaved after the Met, the Pro-Pro-Arg-Glu . . . (see SEQ ID NO:5) sequence allowed for the aminopeptidase pepXP to cleave after the second proline, leaving the arginine as the first amino acid (FIG. 2).

The intermediate construct pRAB-48 was created by cloning the synthetic linker RO113/114

5'--TATGCCGCCGCGTGAAACCATCGAATCCCTGAGCT--3'
   (see SEQ ID NO:6)

3'--ACGGCGGCGCACTTTGGTAGCTTAGGGAC--5' (see SEQ ID NO:7)

into pS637 at the NdeI/SacI sites (note: sequence for proline is underlined). Once again, the new construct was sequenced to verify the presence of the second proline (FIG. 5).

Figure 6:
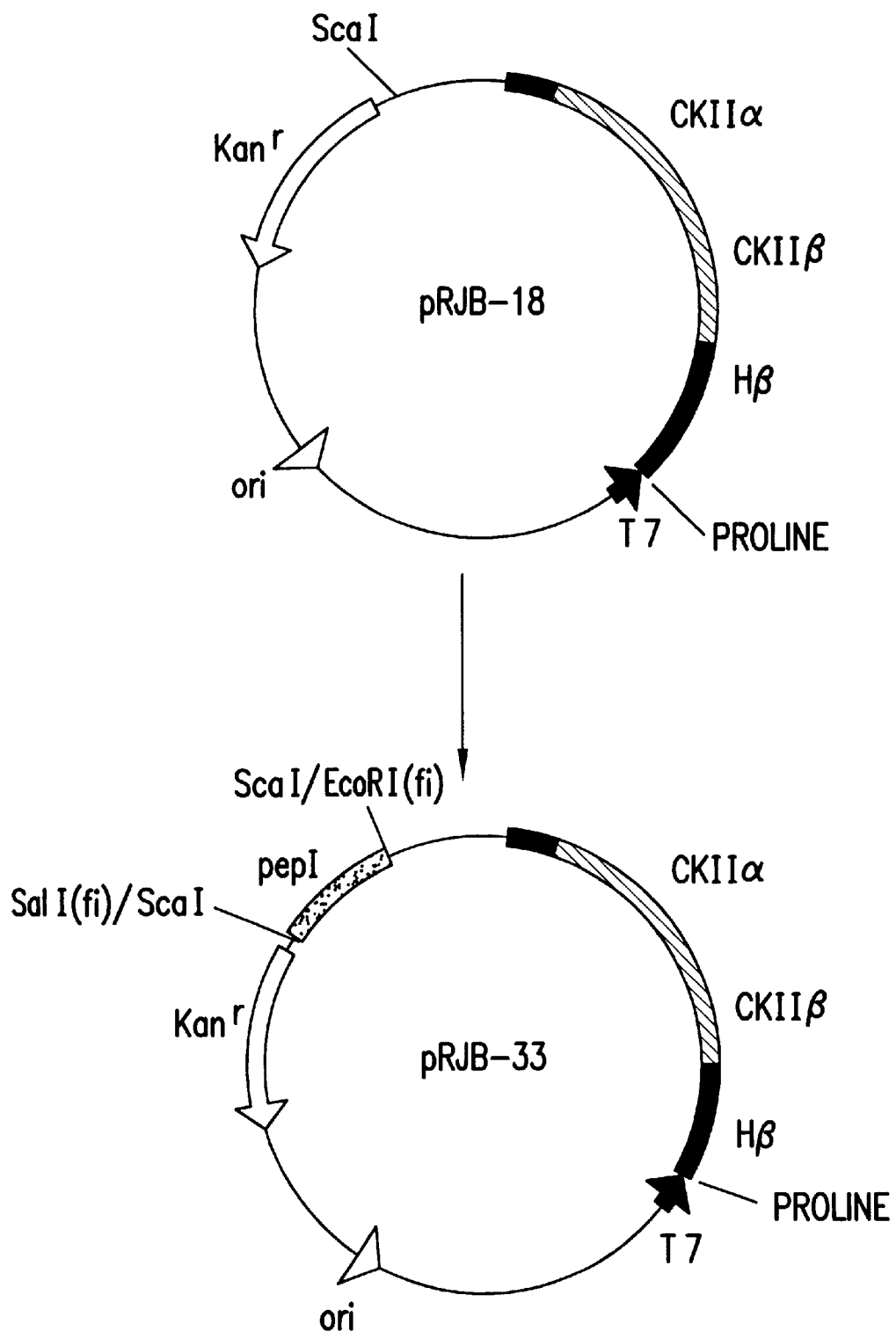
FIG. 6 illustrates the cloning of the pepI gene.

The marker gene in pRAB-30 was changed from ampicillin resistance to kanamycin resistance. An EcoRI Genblock (Pharmacia, Piscataway, N.J.) encoding for kanamycin resistance was filled in at EcoRI with Klenow enzyme (Strategene, La Jolla, Calif.), to create blunt ends. pRAB-30 was cut at PvuI, treated with T4 DNA polymerase to create blunt ends, and ligated to the blunt ended kanamycin Genblock. The resultant clone was designated pRJB-18 (see FIG. 6).

EXAMPLE II

Isolation and Cloning of a Proline Iminopeptidase Gene (pepI) and an Aminopeptidase Gene (pepXP)

The gene sequence of a proline iminopeptidase from Lactobacillus spp., (pepI), has been previously published (Klein, et al., *Microbiology* 140:1133–39 (1994)). *Lactobacillus delbrueckii* subsp. lactis ATCC 4797 was grown at 37° C. in Lactobacillus MRS broth (Difco, Detroit, Mich.), to an optical density (O.D.) of 0.5–0.6 at $A_{660}$. Chromosomal DNA from 50 ml of *L. delbrueckii* was extracted by the method described in Leenhouts, et al. (*Appl. and Envir. Micro.* 55:394–400 (1989)). The DNA was quantitated using a spectrophotometric method (Sambrook, et al., *Molecular Cloning: A Laboratory Manual*, 2nd edition. Cold Spring Harbor Press. New York, 1989). Optimal reaction conditions for Polymerase Chain Reaction (PCR) to amplify the gene fragment were determined using different amounts of DNA. Two primer sets were used: RO117 (5'--TCAGAGGAATTCAAGATGCAAATCACAGAAAAATA--3' (see SEQ ID NO:8)), which introduced an EcoRI site at the 5' end of the gene and RO118 (5'--GTGTCCGTCGACCTAGTCCTGGCTGATTAACCAGT--3' (see SEQ ID NO:9)) which incorporated a SalI site at the 3' end of the pepI gene. UlTma DNA polymerase (Perkin Elmer, Foster City, Calif.) was used in the PCR reaction to ensure the fidelity of the DNA sequence in the standard reaction (Ausubel, et al., *Short Protocols in Molecular Biology*, 2nd edition. Greene Publ. Assocs. and John Wiley & Sons. New York, 1992). The reaction conditions were as follows: an initial melt step at 95° C. for 5 minutes followed by 25 cycles of 94° C. for 30 seconds, 55° C. for 2 minutes, and 72° C. for 2 minutes. The optimized reaction was repeated on a larger scale, and the pepI gene fragment of 900 bases was purified from an agarose gel using the QiaQuick gel purification kit (Qiagen, Chatsworth, Calif.). The PCR fragment (pepI) cut with EcoRI/SalI ligated to the vector pET-24a(+), under the control of a T7 promoter, was designated pRJB-31.

The pepI gene fragment was cut out of its intermediate vector, pRJB-31, as an EcoRI and SalI DNA fragment, separated by agarose gel electrophoresis, and the fragments purified by QiaQuick Gel purification kit (Qiagen). The ends of the fragments were treated with T4 DNA polymerase (Boehringer Mannheim, Indianapolis, Ind.) to create blunt ends. The final expression clone was prepared by cutting pRJB-18 at ScaI, treating with phosphatase (Boehringer Mannheim, Indianapolis, Ind.) and using a Blunt Ligation efficiency kit (5 Prime→3 Prime, Boulder, Colo.) with the blunt pepI fragment. The resulting clone was designated pRJB-33 (see FIG. 6).

Figure 7:
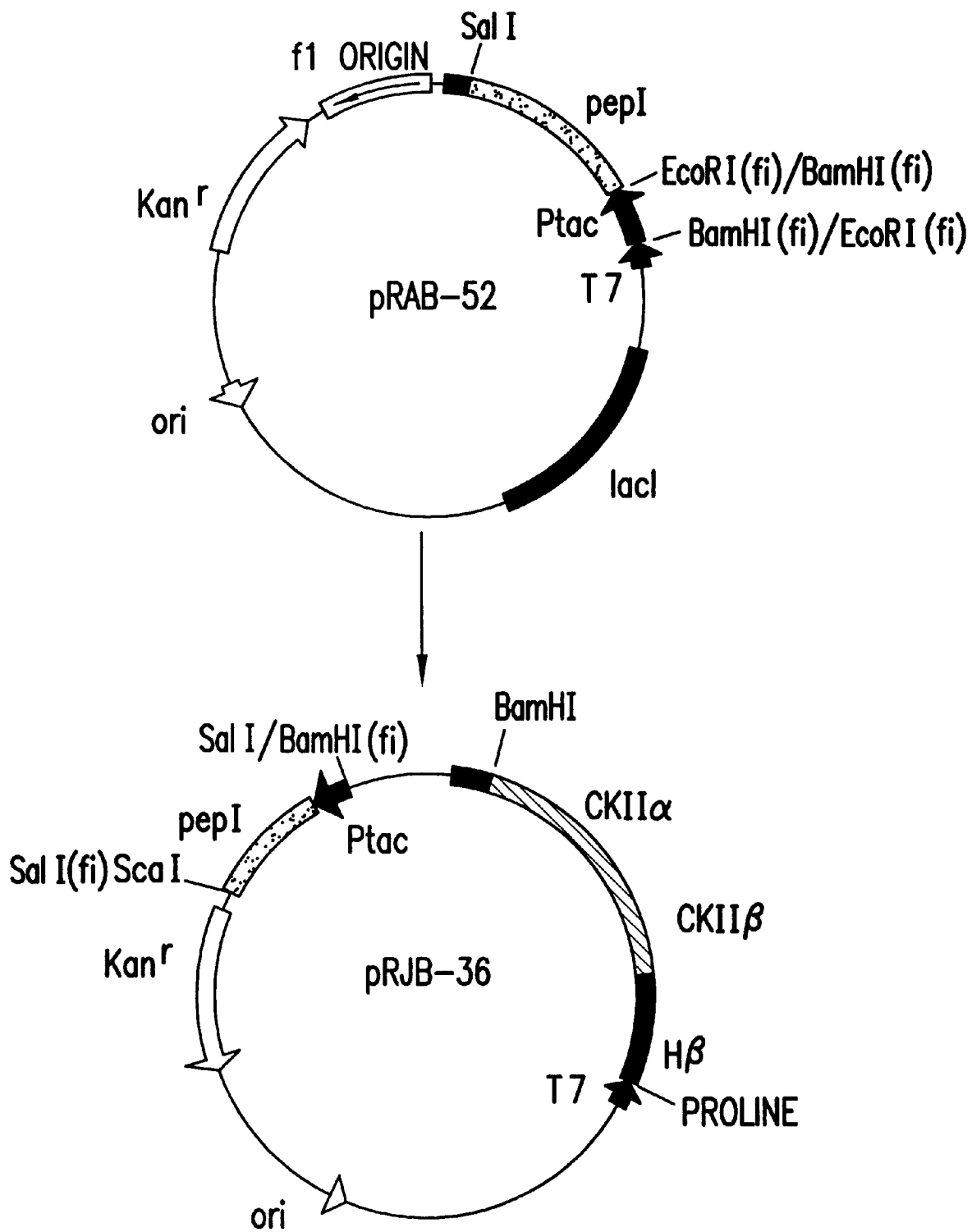
FIG. 7 illustrates the addition of the Ptac promoter to the pepI gene.

To increase the amount of proline aminopeptidase produced in the cell, it was decided that an *E. coli* promoter should be used. The Ptac promoter was isolated from pKK223-3 (Pharmacia) as a BamHI fragment, and the ends were treated with T4 DNA polymerase to create blunt ends. An intermediate clone, pRAB-52, was created by cutting pRJB-31 (pepI) with EcoRI, treating with T4 DNA polymerase to create blunt ends, and ligating it to the blunt Ptac fragment (see FIG. 7). The Ptac/pepI was isolated from pRAB-52 as a BamHI/SalI fragment, treated with T4 DNA polymerase to created blunt ends, and ligated to pRJB-18 at ScaI to produce pRJB-36 (see FIG. 7).

Figure 8:
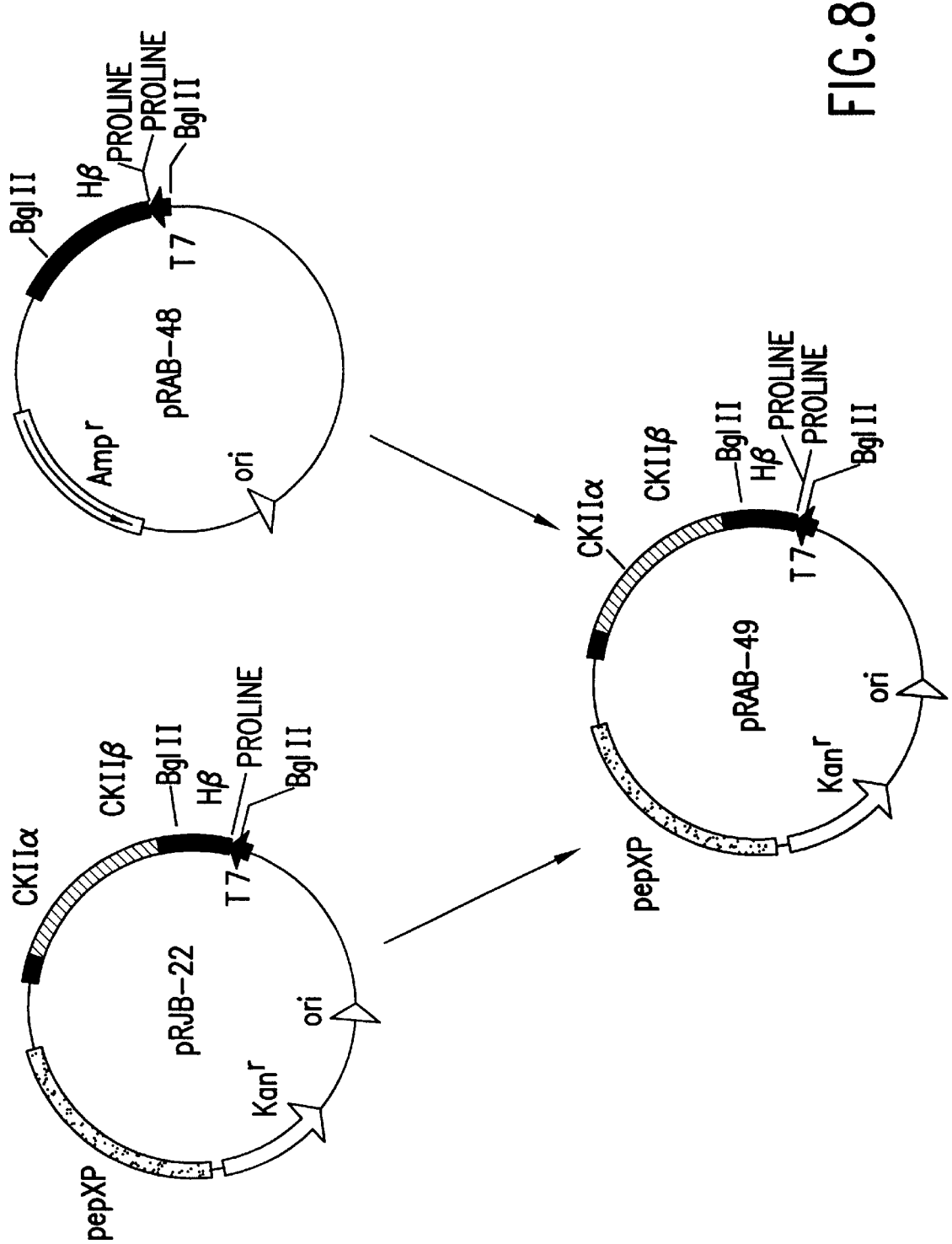
FIG. 8 illustrates the creation of the expression vector pRAB-49 containing the human beta-casein gene with the two additional prolines and the pepXP gene by the combination of elements from the vectors pRAB-48 and pRJB-22.

To isolate the pepXP gene, a culture of *Lactococcus lactis* subspecies lactis ATCC 7962 was inoculated into M-17 (Difco) medium supplemented with lactose at 30° C. until it reached an optical density of 0.6 at $A_{660}$. Approximately 50 ml of culture was used for the chromosomal DNA isolation which is described in Leenhouts, et al. (*Appl. and Envir. Micro.* 55:394–400 (1989)). The DNA concentration was measured by a spectrophotometric method (Sambrook, et al., *Molecular Cloning: A Laboratory Manual*, 2nd edition. Cold Spring Harbor Press. New York, 1989). Optimal reaction conditions for polymerase chain reaction (PCR) (Ausubel et al., supra (1992)) to amplify the gene fragment were determined using different amounts of DNA. UlTma DNA polymerase (Perkin Elmer) was used to ensure the fidelity of the DNA sequence in the standard reaction. The reaction conditions were as follows: an initial melt step at 95° C. for 5 minutes followed by 25 cycles of 72° C. for 3 minutes, 95° C. for 1 minute, and 47° C. for 2 minutes. The primers used in pepXP isolation were RO37 5'--AAAGTAGGATCCTGTTTATTACGGAGGATTTAAAATGCG--3' (see SEQ ID NO:10), which contains a BamHI site for the 5' end of the gene, and RO35, 5'--GTCGCGGTCGACTTAATTTTTCACACTTTCAATAGGAAT--3' (see SEQ ID NO:11), which incorporated a SalI site at the 3' end of the gene. The putative pepXP fragment of 2400 bases (Mayo et al., *Applied and Environmental Microbiology* 57:38–44 (1991)) was purified from an agarose gel. The PCR fragment cut with BamHI and SalI was ligated to an intermediate vector pUC18, and the resultant construct was designated as pRJB-14. The pepXP was cut out of pRJB-14 as a BamHI/SalI fragment and cloned into the pET-24a(+) vector. This new construct was designated as pRAB-27. To create an intermediate expression construct, pRJB-22, the pepXP SmaI/SalI fragment, treated to create blunt ends, was cloned into the ScaI site of pRJB-18 (FIG. 8). The expression construct, pRAB-49 (FIG. 8), was created from pRJB-22 by cutting with BglII, and the fragment containing the human beta-casein gene was replaced by the BglII fragment from pRAB-48.

Figure 9:
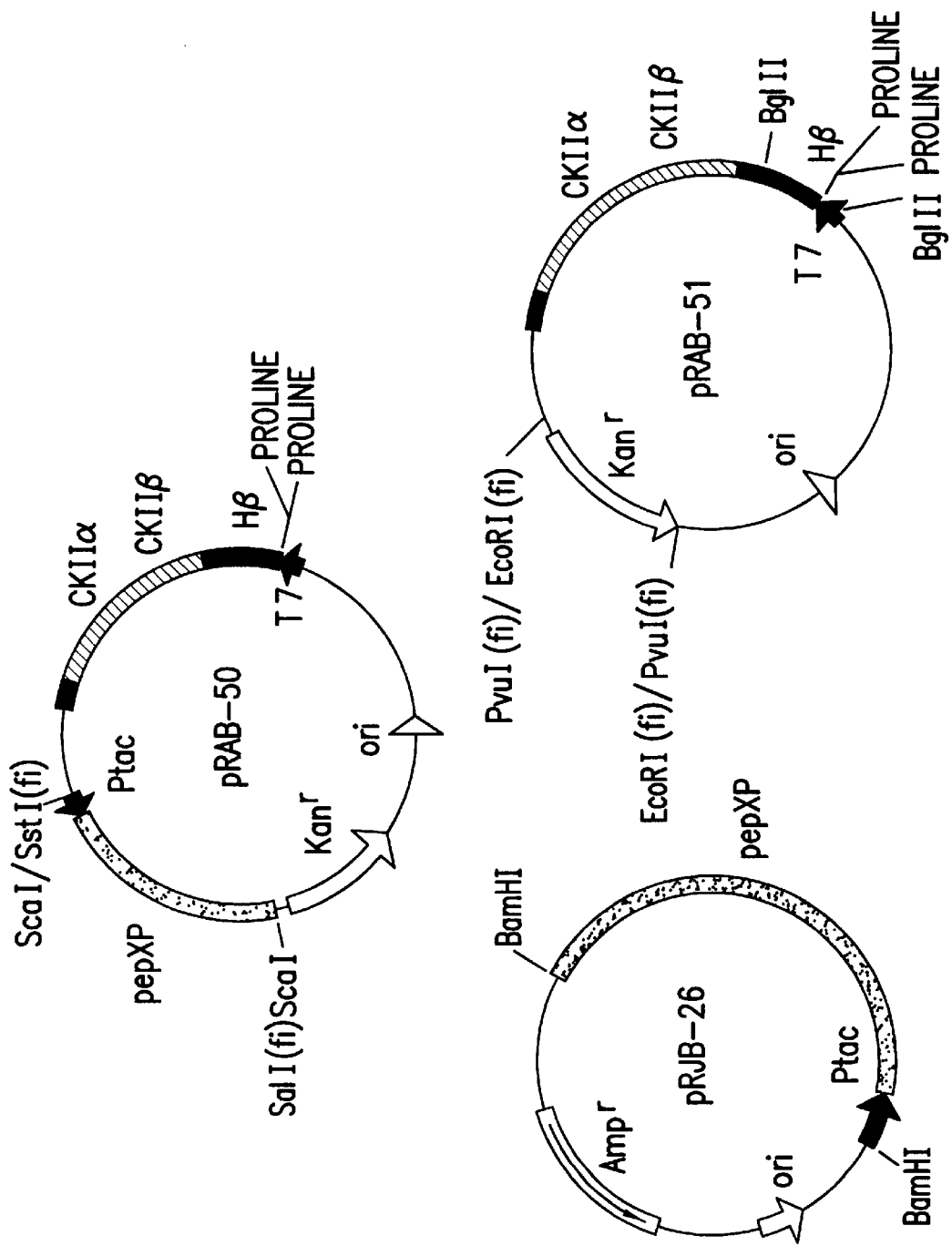
FIG. 9 illustrates the vector pRAB-50 which contains the Ptac promoter linked to the pepXP gene. pRAB-51 contains the human beta-casein sequence with two additonal prolines, while pRJB-26 contains the Ptac linked to the pepXP gene.

In order to optimize the production of pepXP, an additional promoter Ptac was utilized. The Ptac BamHI fragment, isolated from pKK223-3 (Pharmacia), was cloned into the BamHI site of pRJB-14 to create pRJB-26. pRJB-28 was created by placing the Ptac/pepXP SstI/SalI blunt ended fragment from pRJB-26 into the plasmid pRJB-18 at the ScaI site. To generate the construct pRAB-50 (FIG. 9), pRJB-28 was cut with BglII, and the fragment was replaced by the BglII fragment from pRAB-48, which contained two extra prolines. An additional construct, designated pRAB-51 (FIG. 9), was generated from pRJB-18 by removing the BglII fragment from the beta-casein gene and replacing it with the BglII fragment from pRAB-48. pRAB-51 (kanamycin resistant, human beta-casein gene with two additional prolines) was cotransformed with pRJB-26 (ampicillin resistant, with pepXP expressed under the control of the Ptac promotor), into the E. coli strain HMS174 (DE3) as a two plasmid system.

EXAMPLE III

Expression of Beta-Casein in E. coli K-12

The constructs pRAB-30, pRJB-33 and pRJB-36 were transformed into the E. coli K-12 host HMS174(DE3) (Novagen, Madison, Wis.). The E. coli hosts containing the plasmid were grown at 30° C. to an O.D. of 0.5 to 0.9 at $A_{600}$. To induce the production of the recombinant protein, lactose was added to a final concentration of 1.7% (w/v) and the growth continued 16–20 hours. Aliquots of 1 ml were centrifuged at 11,000×g in a microcentrifuge to pellet the bacteria, the supernatant decanted and the pellet resuspended in either 200 μl or 1 ml of 1 X SDS-PAGE sample buffer (Laemmli, Nature 227:680–685 (1970)).

The cell lysates were separated by gel electrophoresis in a discontinuous system on a 10–20% SDS-polyacrylamide pre-cast gel (Integrated Separations System, Natick, Mass.).

Figure 10:
FIG. 10 illustrates recombinant beta-casein production levels with a Western blot developed with antibody t0 human beta-casein. N refers to native human beta-casein isolated from human milk. R denotes purified non-phosphorylated recombinant human beta-casein. Numbers refer to the plasmids used: 33 (pRJB-33) and 36 (pRJB-36). An equal volume of lysate was loaded for each lane.

The recombinant beta-casein production level from pRJB-33 and pRJB-36 (Lanes 2 and 3, FIG. 10) appear to be equivalent. The Western blot (FIG. 10) developed with antibody to beta-casein, exhibited strong bands of similar molecular weight to native human beta-casein (see Lane 1) isolated from human milk and the recombinant nonphosphorylated beta-casein (see Lane 4).

Figure 11:
FIG. 11 represents production of recombinant human beta casein containing two additional proline codons with a Western blot developed with antibody to human beta-casein. N refers to native human beta-casein isolated from human milk. R denotes purified non-phosphorylated recombinant human beta-casein. The numbers refer to the plasmids used: 26/51 (pRJB-26/pRAB51) and 50 (pRAB-50). Approximately twice the volume of lysate was used for pRAB-50 since the amount of total cellular protein was low.

The feasibility of the expression system in which the codons for two prolines had been added to the N-terminus of the beta-casein sequence was tested by comparing expression in E. coli of one vs. two plasmid systems. The constructs pRJB-26 (pepXP) and pRAB-51 (human beta-casein and CKIIβα) were cotransformed into HMS174(DE3). The construct pRAB-50, a single plasmid system containing the genes for human beta-casein and CKIIβα under the control of the T7 promoter and pepXP under the control of the Ptac promoter, was also transformed into HMS174(DE3). The E. coli lysates from induced culture of the double construct pRJB-26/pRAB-51 were compared to the lysates from the single construct pRAB-50. Western blot analysis (FIG. 11) of these lysates using antibody to native human beta-casein showed that there was a dramatic reduction of recombinant beta-casein from the lysate of pRAB-50 as compared to the lysate of pRJB-26/pRAB-51 (lanes 2 and 3).

EXAMPLE IV

Isolation and Characterization of Phosphoforms of Recombinant Beta-Casein

Cells harvested by centrifugation at 7000×g for 10 minutes at 4° C. were frozen on dry ice/ethanol and thawed 3 times to release the recombinant protein (Johnson et al., Bio/Technology 12:1357–1360 (1994)). This method appeared to release a relatively pure sample of recombinant human beta-casein. Following filtration through a 0.45μ membrane, the supernatant was loaded onto an anion exchange Mono Q column (Pharmacia). Resolution of the various phosphoforms of recombinant human beta-casein was achieved using a linear gradient of 0 to 0.5 M NaCl in 20 mM ethanolamine, pH 9.5, 6 M urea over 50 minutes (Hansson, et al., Prot. Exp. and Purif. 4:373–381 (1993)). Phosphoforms were identified by their time of elution when compared to the purified native human milk beta-casein. The presence of recombinant beta-casein was verified in putative phosphoform fractions by separation on a 12.5% SDS-PAGE Phast gel (Pharmacia) by staining with Coomassie Blue. After confirmation of the phosphoforms, the pertinent fractions were dialyzed against water, dried, and analyzed for the N-terminus sequence.

Figure 12A:
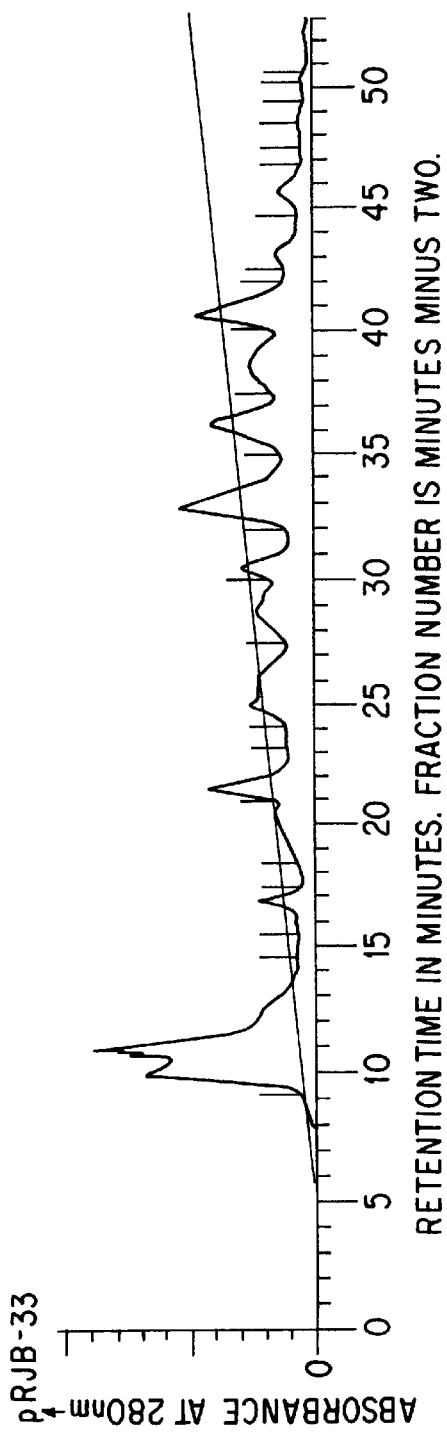
FIG. 12 illustrates the separation of the phosphoforms of recombinant phosphorylated beta-casein from pRJB-36 and pRJB-33 by ion exchange chromatography. The level of phosphorylation is noted on the peak of the human milk beta-casein phosphoform chromatogram.
Figure 12B:
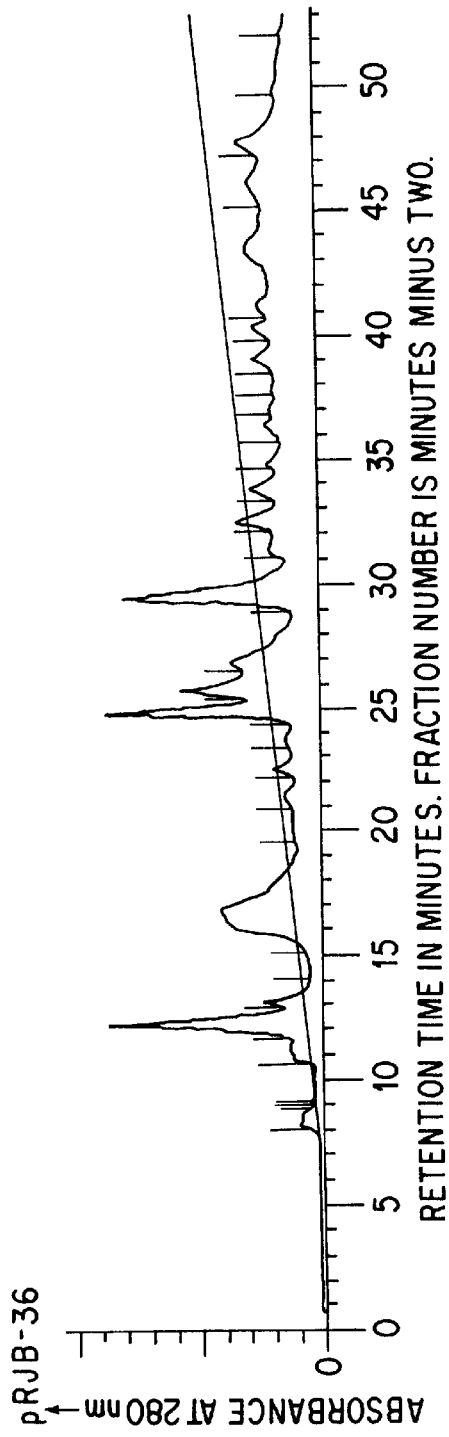
Figure 12C:
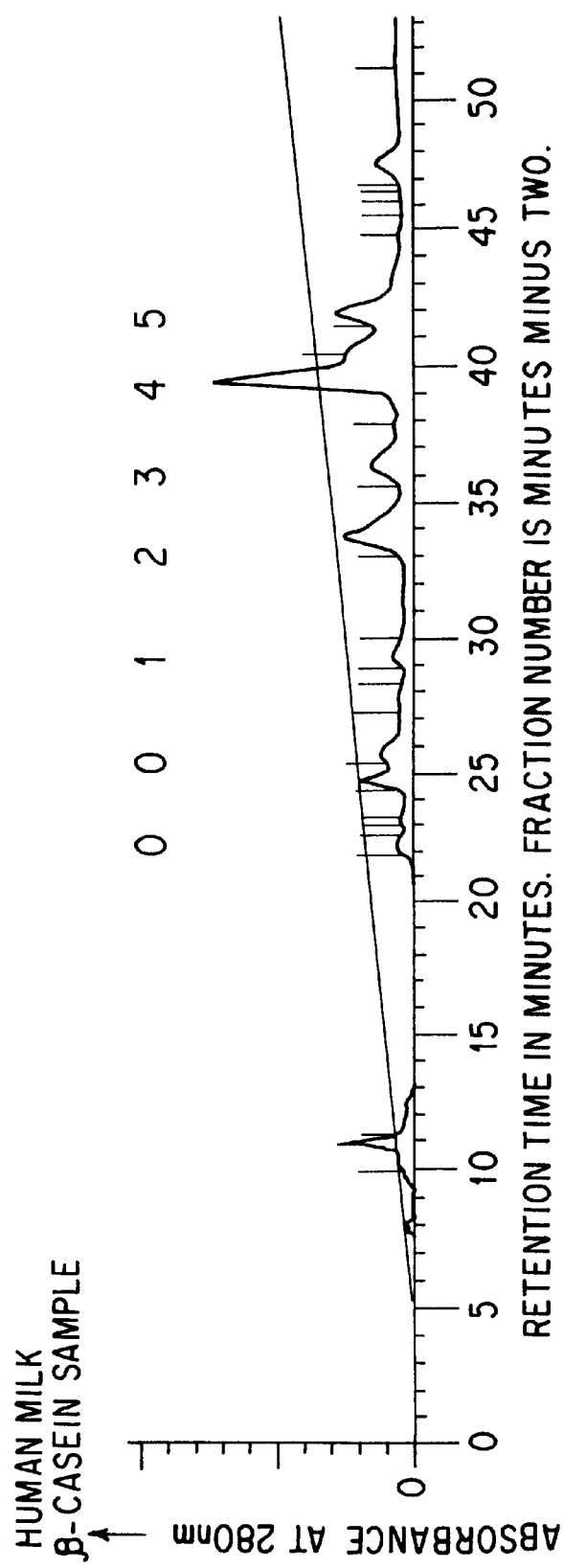

To characterize the phosphoforms of the recombinant phosphorylated beta-casein from pRJB-33 and pRJB-36, the lysates prepared as previously described were resolved on an anion exchange column. All six phosphoforms, non-through penta-phosphorylated, were detected for recombinant human beta-casein. The level of phosphorylation is noted on the peak of the human milk beta-casein phosphoform chromatogram in FIG. 12. (Note that there were two peaks for 0 phosphates.) There appear to be two isoforms of the non-phosphorylated beta-casein. This was also observed by Hansson et al., supra (1993)).

By comparing the chromatogram of the native human beta-casein to the recombinant beta-casein, each peak was putatively assigned a level of phosphorylation.

FIG. 13 illustrates the various phosphoforms of recombinant human beta-casein produced from the two construct system, pRJB-26/pRAB-51. There are peaks obtained from recombinant beta-casein preparation which have the same retention time as the six different phosphoforms of beta-casein found in human milk.

EXAMPLE V

Proline Iminopeptidase Assay

Cells were inoculated from an overnight culture 1:50 to 50 ml of fresh Luria Bertani Broth containing kanamycin. The cells were allowed to grow at 30° C. until the O.D. reached between 0.7 and 1 at $A_{600}$. Lactose was added during bacterial logarithmic growth to a culture of E. coli transformed with pRAB-52 since it contained the inducible promoter, Ptac. The plasmid pRJB-33 contained a promoter for pepI which was constitutive. Each pellet was harvested by centrifugation at 10,000×g for 5 minutes at 4° C. The pellet was sonicated on ice in 50 mM Tris pH 8.0, 1 mM EDTA, and 0.2 mM phenylmethyl sulfonylfluoride (PMSF). The iminopeptidase substrate L-prolyl-p-nitroanilide (pro-pNA; Bachem Bioscience, Inc., King of Prussia, Pa.) was prepared at 6 mM in deionized water with the assistance of sonication. Forty microliters of the substrate solution was added to a cuvette containing 920 μl of 50 mM Tris-HCl pH 8.0 and the contents mixed by inversion. Following a five-minute incubation of the cuvette at 30° C. in a temperature regulated spectrophotometer, 40 μl of cell extract was added to the cuvette and the contents again mixed by inversion. The reaction at 30° C. was monitored for one minute by following the increase in the absorbance at 410 nm. Rates of reaction were calculated by using an extinction coefficient of 9600 (Zevaco et al., Appl. Bacteriol. 68:357–366 (1990)). The proline iminopeptidase activity was determined to be 0.00053 and 0.000042 mmol/min/mg for pRJB-33 and pRAB-52, respectively.

EXAMPLE VI

X-Prolyl Dipeptidyl Aminopeptidase Assay

Induced cultures of HMS174(DE3) containing the desired constructs were disrupted by sonication in 100 mM Tris (pH 8.0), 1 mM EDTA, and 0.2 mM PMSF, and the crude extract was centrifuged to remove the debris. For the cells containing pRAB-27, the resulting supernatant was diluted to 1 mg/ml with the same buffer.

Reactions were run at 23° C. in a final volume of 840 µl containing 100 mM Tris, pH 8.0, 2.8 mM Phe-Pro-β-naphthylamine (Bachem Bioscience Inc., King of Prussia, Pa.) and up to 453 µg to extract. The reactions were initiated by the addition of the Phe-Pro-β naphthylamine substrate and their progress monitored by the increase in absorbance at 340 nm for a duration of one minute.

The extract prepared from HMS174(DE3)(pRAB-27) was found to cleave the Phe-Pro dipeptide of the synthetic substrate Phe-Pro-β-naphthylamine indicating the presence of active X-prolyl dipeptidylaminopeptidase in vitro, at 0.015+/−0.001 mmol/min/mg.

Although 52 µg of the extract prepared from HMS174 (DE3)(pRAB-49) was tested against the synthetic substrate Phe-Pro-β-naphthylamine, the enzyme activity was below the detection limits of the in vitro assay.

EXAMPLE VII

Protein Sequencing

N-terminal sequences were obtained via automated Edman degradation using an Applied Biosystems, Inc. (ABI, Foster City, Calif.) 470A or 473A Protein sequencer with an online ABI analyzer. Five to six cycles were performed on each sample. The analyses were performed at the Protein and Carbohydrate Structure Facility of the University of Michigan Medical School.

Table 1 below illustrates results obtained from sequencing the recombinant lysates purified on the Mono Q column.

TABLE 1

| Plasmid(s) in HMS 174 (DE3) | N-terminal Sequences of Recombinant Phosphorylated Human Beta-Casein | | | | | |
|---|---|---|---|---|---|---|
| | Cycle 1 | Cycle 2 | Cycle 3 | Cycle 4 | Cycle 5 | Cycle 6 |
| pRJB-27 pRAB-30 | Pro | Arg | Glu | Thr | Ile | Glu |
| pRAB-30 | Pro | Arg | Glu | Thr | Ile | Glu |
| pRJB-33 | *Arg | Glu | Thr | Ile | Glu | Ser |
| | X | Arg | Glu | Thr | Ile | Glu |
| pRJB-36 | *Arg | Glu | Thr | Ile | Glu | Ser |
| pRJB-26 pRAB-51 | *X | Glu | Thr | Ile | Glu | Ser |

X = several amino acids; * = correct processing

N-terminal amino acid sequencing of the diphosphate form of recombinant human beta-casein isolated from HMS174(DE3)(pRJB-27/pRAB-30), which contained the pepXP for the aminopeptidase, revealed that the N-terminus of recombinant human beta-casein was proline instead of methionine. N-terminal amino acid sequencing of diphosphorylated recombinant human beta-casein from HMS174 (DE3) (pRAB-30), which lacked aminopeptidase activity, contained an N-terminal proline instead of methionine. Thus, it would appear that within the HMS174(DE3) *E. coli* strain, there is an endogenous methionine aminopeptidase that cleaves the Met from Met-Pro-recombinant human beta-casein.

The single construct pRJB-33 produced the expected sequence of Arg-Glu-Thr-Ile-Glu (see SEQ ID NO:12). The N-terminal sequencing pattern for pRJB-33 indicated that, while the correctly processed sequence of Arg-Glu-Thr-Ile-Glu-Ser (see SEQ ID NO:13) is present, the same sequence appears to start in the second cycle as well. Incomplete processing would be expected to yield a sequence of Pro-Arg-Glu-Thr-Ile (see SEQ ID NO:14). Hence, all recombinant beta-casein molecules may not have undergone N-terminal processing by iminopeptidase, and growth conditions may need to be modified to achieve complete processing of the N-terminus.

The N-terminal sequence of diphosphorylated recombinant beta-casein from the lysate of (pRJB-36) was Arg-Glu-Thr-Ile . . . (see SEQ ID NO:15). This would indicate that the combination of MAP and the proline iminopeptidase had completely cleaved both the methionine and the proline, respectively, from the N-terminus of recombinant beta-casein.

The diphosphorylated species of the beta-casein produced by pRJB-26/pRAB-51 yielded an N-terminal sequence of Arg-Glu . . . The first cycle of this sequence analysis contained several amino acids, a frequently observed situation due to the elution of free amino acids present in the sample; thus, a definitive identification was not possible for the first amino acid. However, the sequence starting at the second amino acid was Glu-Thr-Ile-Ser-Ser . . . (see SEQ ID NO:16), which corresponds to the sequence in human milk beta-casein. This would also indicate that MAP and the x-prolyl dipeptidyl aminopeptidase processed the N-terminus of the recombinant human beta-casein. Isolated fractions from pRAB-50 were not analyzed with regard to N-terminal sequence due to the low levels of beta-casein produced.

EXAMPLE VIII

Electrospray Ionization Mass Spectroscopy

The samples were analyzed on a Finnigan MAT (San Jose, Calif.) TSQ-700 tandem quadrupole mass spectrometer equipped with an electrospray ionization source. The instrument was operated in the +Q1MS mode scanning the quadrupole mass filter from m/z 200–2500 in 7 seconds. The second and third quadrupole mass filters were operated in the rf-only mode allowing transmission of all ions. Samples were prepared at approximately 1 µg/µL (42 pmol/µL) in 5:95 $CH_3CN:H_2O$ containing 0.1% trifluoroacetic acid. A 20 µL aliquot of this solution was injected into an HPLC system containing a reversed phase column (Vydac, C18, 2.1 mm×250 mm, 300 Å) maintained at 35° C. A gradient from 5% to 70% $CH_3CN$ in $H_2O$ containing 0.1% trifluoacetic acid over 70 minutes at 200 µL/min was used to elute the protein. The effluent was split post-column to deliver 8 µL/min to the ESI source which was operated at 4.5 kV and maintained at 200° C. with 55 psi nitrogen sheath gas. The reported masses for FIG. 14 were obtained following deconvolution of the measured electrospray mass spectrum from the primary HPLC peak.

Figure 14A:
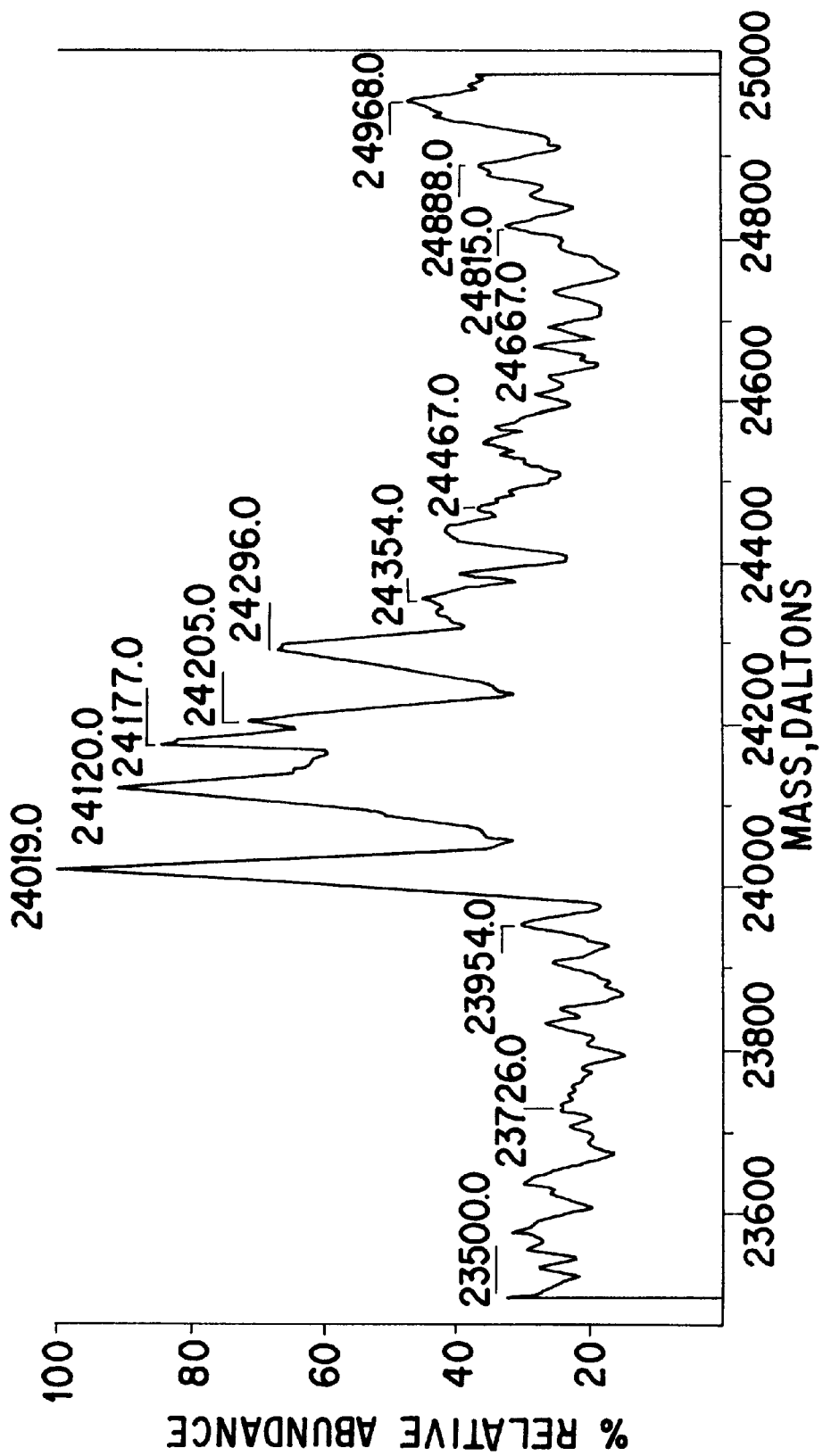
FIG. 14 illustrates electrospray ionization (ESI) of recombinant human beta-casein (top panel) from pRJB-36 and diphosphorylated native beta-casein (bottom panel), confirming the proper processing of the N-terminus of the protein.
Figure 14B:
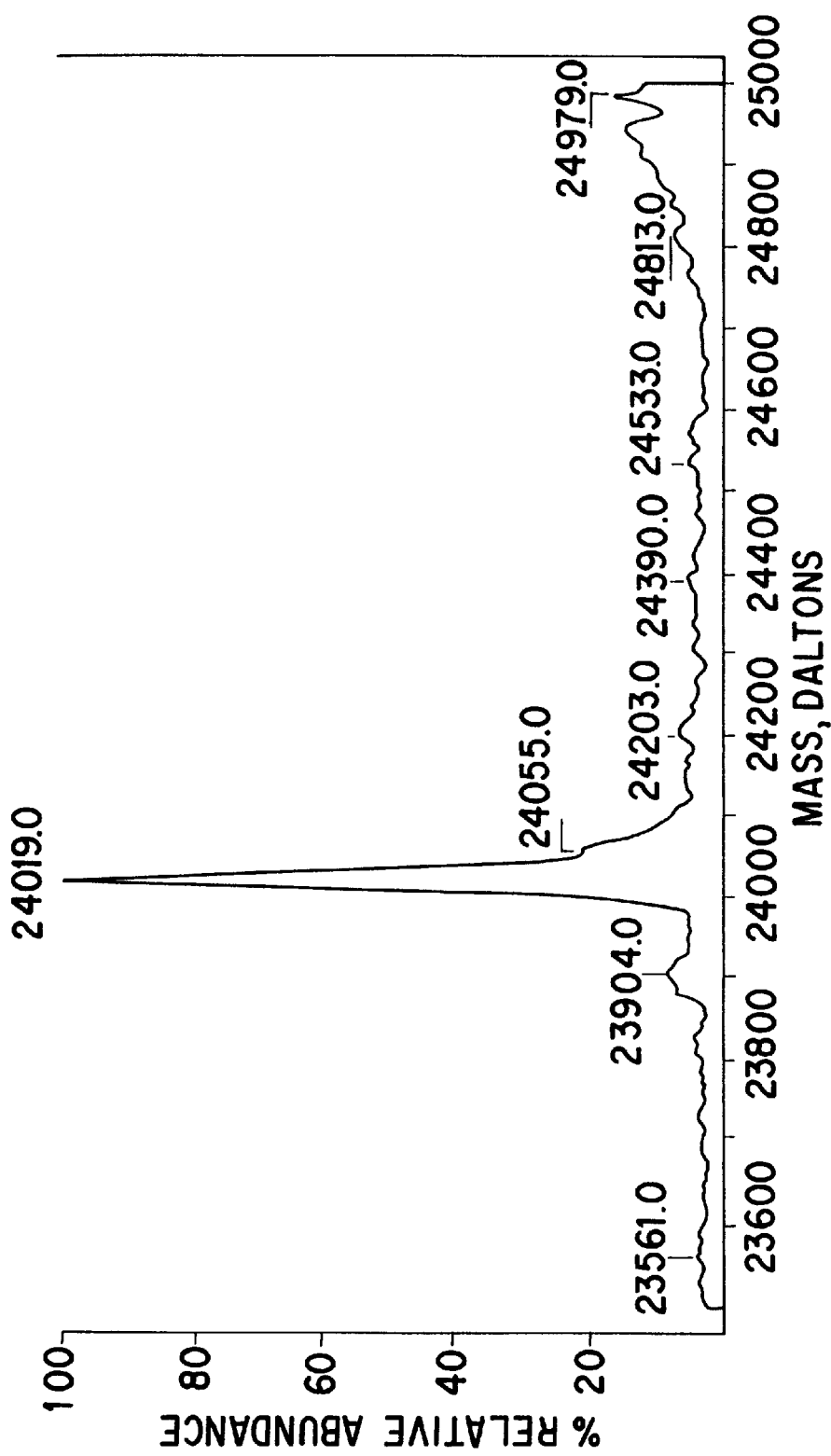

Electrospray ionization (ESI) confirmed that the purified diphosphorylated recombinant human beta-casein from lysate processed from pRJB-36 was correctly processed. As shown in FIG. 14, both the recombinant (top panel) and native (bottom panel) diphosphorylated human beta-casein yielded a signal of 24019 daltons which matches, within the limits of experimental error, the theoretical weight of 24018 daltons. Signals of other than 24019 daltons indicate the presence of additional proteins in the fraction.

The remaining samples were analyzed on a Finnigan (San Jose, Calif.) MAT TSQ70 tandem quadrupole mass spectrometer equipped with an Analytica of Branford (Branford, Conn.) electrospray ionization source. The instrument was operated in the +Q3MS mode scanning the quadrupole mass filter from m/z 200–1900 in 4 seconds. The first and second quadrupole mass filters were operated in the rf-only mode allowing transmission of all ions. Samples were prepared at ca. 4 pmol/$\mu$l in 1:1 MeOH:$H_2O$ containing 0.5% HOAc, and infused into the mass spectrometer at 0.8 $\mu$l/min using a Harvard Apparatus 22 syringe pump. The reported molecular masses were obtained following deconvolution of the measured electrospray mass spectrum.

Figure 15:
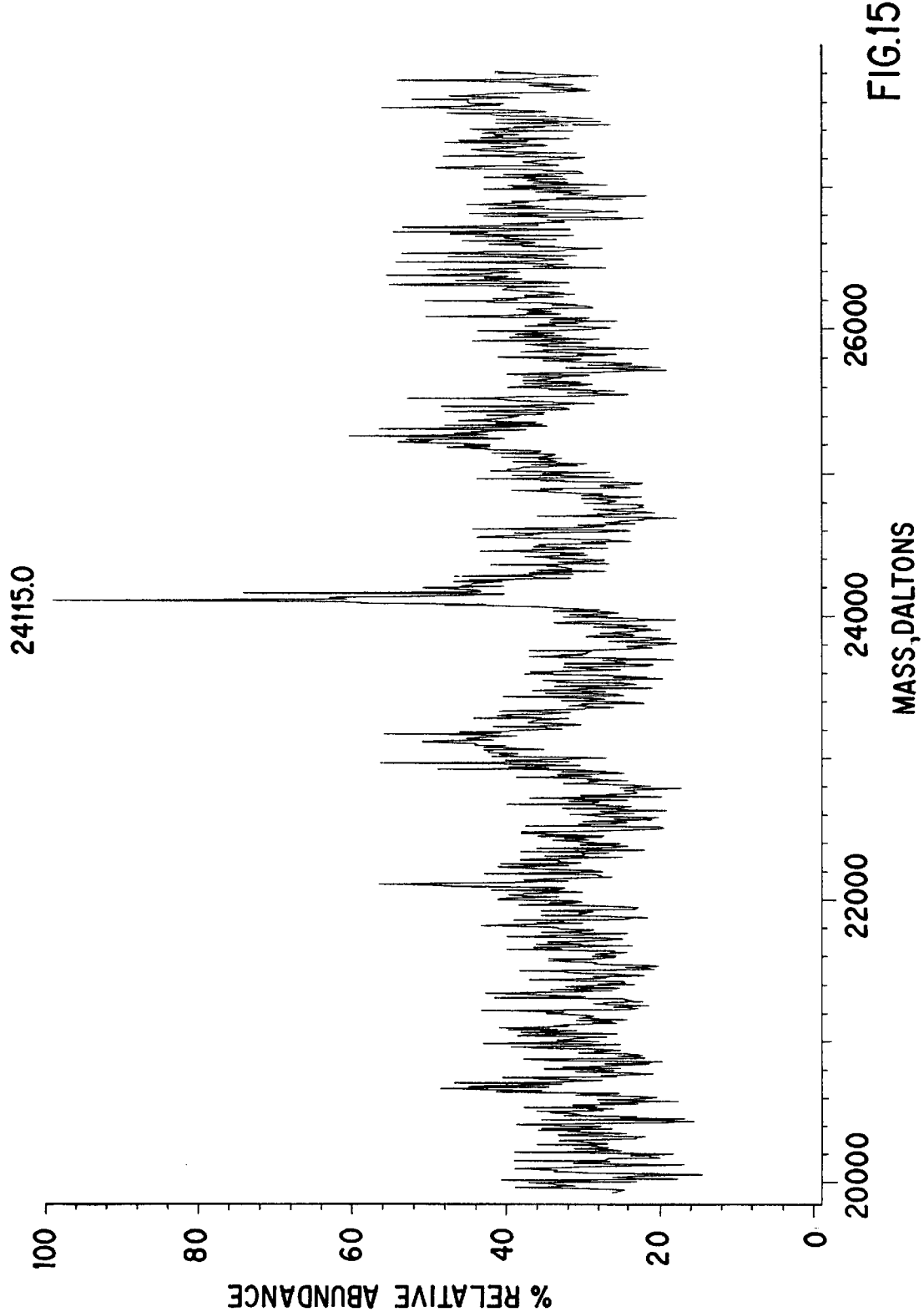
FIG. 15 shows the ESI of disphosphorylated recombinant human beta-casein isolated from coexpression of pRAB-30/pRAB-27, confirming the activity of the endogenous *E. coli* methionine aminopeptidase which cleaved methionine from proline at the N-terminus of the protein.

Electrospray ionization also confirmed the assignment of phosphorylation state of the isolated recombinant human beta-casein fractions from coexpression of pRAB-27/pRAB-30 and the presence of the N-terminal proline in three of the fractions. As shown in FIG. 15, fraction 24 yielded a signal of 24,115 daltons which, within the limits of experimental error, matches the expected molecular weight for diphosphorylated recombinant human beta-casein possessing an extra proline residue. Signals of other than 24,115 daltons in the spectrum represent artifacts of the analyte. ESI spectra of fractions 27 and 28 indicated the presence of proteins of an average molecular weight (N=2) of 24,272.5 and 24,353.5 daltons, respectively (data not shown). Again, within the limits of error, these molecular weights match those expected for tetra- and pentaphosphorylated recombinant human beta-casein with an additional proline residue present.

ESI was used to determine the extent of N-terminal processing for pRAB-49. Analysis of diphosphorylated molecules yielded an average molecular weight (N=6) of 24,222+/−25 daltons (data not shown), consistent with a protein sequence of Pro-Pro-Arg-Glu . . . after removal of Met by MAP from *E. coli*. The low levels of aminopeptidase contributed to the lack of processing at the N-terminus of recombinant human beta-casein produced from pRAB-49.

What is claimed is:

1. A method of producing recombinant beta-casein in vivo comprising the steps of:
   a) constructing a vector comprising: i) a nucleic acid sequence encoding beta-casein and ii) a nucleic acid sequence encoding a peptidase, wherein said beta-casein comprises at least one terminal amino acid not present in the native, mature form of said beta-casein and wherein said nucleic acid sequence encoding said beta-casein is operably linked to a promoter;
   b) introducing said vector into a host cell under time and conditions sufficient to allow for expression of said recombinant beta-casein, wherein said host cell produces an endogenous peptidase which completely cleaves one or more of said N-terminal amino acids of said beta-casein.

2. The method of claim 1 wherein said peptidase encoded by said nucleic acid sequence of step (a) is selected from the group consisting of iminopeptidase and aminopeptidase.

3. The method of claim 2 wherein said iminopeptidase is encoded by gene pepI and said aminopeptidase is encoded by gene pepXP.

4. The method of claim 1 wherein said endogenous peptidase is methionine aminopeptidase.

5. The method of claim 1 wherein said beta-casein is phosphorylated human beta-casein.

6. The method of claim 1 wherein said host cell is selected from the group consisting of a eucaryotic cell and a procaryotic cell.

7. The method of claim 6 wherein said procaryotic cell is *Escherichia coli*.

8. The method of claim 1 wherein said at least one N-terminal amino acid is selected from the group consisting of methionine and proline.

9. A vector comprising: a) a nucleic acid sequence encoding beta-casein and b) a nucleic acid sequence encoding a peptidase, wherein said beta-casein comprises at least one N-terminal amino acid not present in the native, mature form of said beta-casein and wherein said nucleic acid sequence encoding said beta-casein is operably linked to a promoter.

10. The vector of claim 9 wherein said at least one N-terminal amino acid is selected from the group consisting of methionine and proline.

11. The vector of claim 9 wherein said vector is selected from the group consisting of a plasmid, a bacteriophage, and a cosmid.

12. A host cell containing a vector, wherein said vector comprises a) a nucleic acid sequence encoding beta-casein and b) a nucleic acid sequence encoding a peptidase, wherein said beta-casein comprises at least one N-terminal amino acid not present in the native, mature form of said beta-casein and wherein said nucleic acid sequence encoding said beta-casein is operably linked to a promoter, and wherein said host cell encodes an endogenous peptidase which completely cleaves one or more of said at least one N-terminal amino acids of said beta-casein.

13. The host cell of claim 12 wherein said peptidase encoded by said nucleic acid sequence is selected from the group consisting of iminopeptidase and aminopeptidase.

14. The host cell of claim 13 wherein said iminopeptidase is encoded by gene pepI and said aminopeptidase is encoded by gene pepXP.

15. The host cell of claim 12 wherein said endogenous peptidase is methionine aminopeptidase.

16. The host cell of claim 12 wherein said host cell is selected from the group consisting of a eucaryotic cell and a procaryotic cell.

17. The host cell of claim 16 wherein said procaryotic cell is *Escherichia coli*.

18. The host cell of claim 12 wherein said at least one N-terminal amino acid is selected from the group consisting of methionine and proline.

* * * * *